United States Patent [19]

Chorvat et al.

[11] 4,053,476
[45] Oct. 11, 1977

[54] 7-AZA-6-ALKOXY-1-TETRALONES

[75] Inventors: Robert J. Chorvat, Arlington Heights; Raphael Pappo, Skokie, both of Ill.

[73] Assignee: G. D. Searle & Co., Chicago, Ill.

[21] Appl. No.: 712,449

[22] Filed: Aug. 9, 1976

Related U.S. Application Data

[63] Continuation-in-part of Ser. No. 543,027, Jan. 22, 1975, Pat. No. 4,012,391, which is a continuation-in-part of Ser. No. 467,217, May 6, 1974, Pat. No. 4,007,192, which is a continuation-in-part of Ser. No. 596,509, Aug. 16, 1975, Pat. No. 3,994,774.

[51] Int. Cl.$^2$ .......................................... C07D 217/24
[52] U.S. Cl. .................................................. 260/289 D
[58] Field of Search .................................... 260/289 D

*Primary Examiner*—Donald G. Daus
*Assistant Examiner*—David B. Springer
*Attorney, Agent, or Firm*—Joy A. Serauskas

[57] ABSTRACT

The preparation of 7-aza-6-alkoxy-1-tetralones which originates with dihydroresorcinol is disclosed herein. The subject compounds are useful intermediates in the synthesis of various compounds which possess valuable pharmacological properties.

2 Claims, No Drawings

7-AZA-6-ALKOXY-1-TETRALONES

The present application is a continuation-in-part of copending applications Ser. No. 543,027 filed Jan. 22, 1975 now U.S. Pat. No. 4,012,391, issued Mar. 15, 1977 which is a continuation-in-part of Ser. No. 467,217 filed May 6, 1974, now U.S. Pat. No. 4,007,192 issued Feb. 8, 1977 and Ser. No. 596,509 filed Aug. 16, 1975; now U.S. Pat. No. 3,994,774, issued Nov. 30, 1976.

The present invention relates to novel compounds of the formula

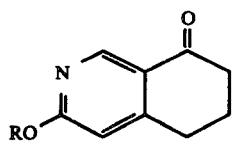

wherein R is an alkyl radical containing 1 to 4 carbon atoms. The alkyl radicals are typified by methyl, ethyl, propyl and butyl and the branched-chain isomers thereof. A preferred embodiment of the present invention as set out in formula I is one in which R is methyl.

The compounds of the present invention are prepared from a novel process which utilizes dihydroresorcinol as the starting material. Dihydroresorcinol is allowed to react with a chlorinating reagent such as phosphorous trichloride to afford 3-chloro-2-cyclohexen-1-one. Reaction with cyanoacetamide and sodium hydride results in α-cyano-3-oxo-1-cyclohexen-1-acetamide, which is then contacted with a dialkylformamide acetal, for example, dimethylformamide diethylacetal or dimethylformamide dineopentyl acetal, or trialkylorthoformate, for example triethylorthoformate, to produce 2,3,5,6,7,8-hexahydro-3,8-dioxo-4-isoquinolinecarbonitrile. Elimination of the cyano group is effected by heating with hydrobromic acid, thus affording 2,3,5,6,7,8-hexahydro-3,8-isoquinolinedione. Heating with an alkyl halide produces the corresponding 6-alkoxy-7-aza-1-tetralone together with the N-alkylated derivative. Typically, 2,3,5,6,7,8-hexahydro-3,8-isoquinolinedione is heated in benzene at the reflux temperature with methyl iodide and silver carbonate to yield 7-aza-6-methoxy-1-tetralone together with 2-methyl-2,3,5,6,7,8-hexahydro-3,8-isoquinolinedione.

Specifically these compounds are useful in preparing dl-2-aza-3-methoxyestra-1,3,5(10),8,14-pentaen-17-one; dl-2-aza-3-methoxyestra-1,3,5(10),8,14-pentaen-17β-ol; dl-2-aza-3-methoxyestra-1,3,5(10),8-tetraen-17-one; dl-2-aza- 3-methoxyestra-1,3,5(10),8-tetraen-17β-ol; 2-aza-3-methoxy-11β-methylestra-1,3,5(10)-trien-17β-ol; 2-aza-3-methoxy-11β-methyl-17β-methylestra-1,3,5(10)-trien-17β-ol. These compounds possess valuable hypolipemic activity.

The compounds of the present invention are also useful in preparing 3-methoxy-2-azanaphthalene-7-acetic acid, ethyl 3-methoxy-2-azanaphthalene-7-acetate, 3-methoxy-2-azanaphthalene-7α-methylacetic acid, methyl 3-ethoxy-2-azanaphthalene-7-acetic acid and 3-methoxy-2-azanaphthalene-7α-methyl-α-ethylacetic acid. These aforesaid compounds are useful intermediates for other biologically active compounds. For instance, the corresponding aldehydes and alcohols are potent anti-inflammatory compounds.

Compounds of the present invention are converted into useful hypolipemic compounds by the following reaction sequence.

The 7-aza-6-methoxy-1-tetralone is reacted with vinyl magnesium chloride to give 7-aza-6-methoxy-1-vinyl-1-tetralol, which is contacted with a 2-(lower alkyl)cyclopentane-1,3-dione, such as 2-methylcyclopentane-1,3-dione, in the presence of a basic catalyst such as triethylamine to afford 5,6,7,8-tetrahydro-3-methoxy-8-[(2-methyl-1,3-dioxocyclopent-2-yl)ethylidene]isoquinoline. Alternatively, the tetralol is converted to the isothiouronium salt, which is reacted with the dione to afford the latter product. Cyclization of the latter diketone, suitably in the presence of p-toluenesulfonic acid, results in dl-2-aza-3-methoxy-estra-1,3,5(10),8,14-pentaen-17-one. Catalytic hydrogenation, using a palladium-on-calcium carbonate catalyst effects saturation of the 14-double bond, thus producing dl-2-aza-3-methoxyestra-1,3,5(10),8-tetraen-17-one, while chemical reduction, for example with sodium borohydride, converts the 17-keto group, thus yielding dl-2-aza-3-methoxyestra-1,3,5(10),8,14-pentaen-17β-ol. The 14-double bond of the latter substance is catalytically reduced, using a palladium-on-calcium carbonate catalyst, to yield dl-2-aza-3-methoxyestra-1,3,5(10),8-tetraen-17β-ol, which is allowed to react with sodium in liquid ammonia to afford dl-2-aza-3-methoxyestra-1,3,5(10)-trien-17β-ol.

The 11β-alkyl compounds are produced by reacting 7-aza-6-methoxy-1-tetralone with a solution containing butyl lithium and 2-bromo-3-dimethylaminopropene to yield N,N-di-methyl-N-(2-[5,6,7,8-tetrahydro-8-hydroxy-3-methoxyisoquinol-8-yl]prop-2-en-1-yl)amine. The hydroxyl substituent is removed with a phosphorous oxyhalide, such as phosphorous oxychloride in pyridine or in concentrated sulfuric acid, to yield the N,N-dimethyl-N-(2-[5,6-dihydro-3-substituted-isoquinol-8-yl]alk-2-en-1-yl)amine. For example, N,N-dimethyl-N-(2-[5,6,7,8-tetrahydro-8-hydroxy-3-methoxyisoquinol-8-yl]-prop-2-en-1-yl)amine is contacted with phosphorous oxychloride in pyridine to obtain N,N-dimethyl-N-(2-[5,6-dihydro-3-methoxyisoquinol-8-yl]prop-2-en-1-yl)amine. Quaternarization of the amines with an alkyl halide, e.g. methyl iodide, yields the quaternary salts, which are subsequently reacted with silver oxide and then with 2-(lower alkyl)cyclopentane-1,3-dione to yield the appropriate 5,6-dihydro-3-substituted-8-[3-(2-methyl-1,3-dioxocyclopent-2-yl)alk-1-en-2-yl]isoquinoline. In that manner, the aforementioned N,N-dimethyl-N-(2-[5,6-dihydro-3-methoxyisoquinol-8-yl]prop-2-en-1-yl)amine is treated with methyl iodide to afford the corresponding trimethyl ammonium iodide. Subsequent treatment with silver oxide and 2-(lower alkyl)cyclopentane-1,3-dione produces 5,6-dihydro-3-methoxy-8-[3-(2-methyl-1,3-dioxocyclopent-2-yl)-prop-1-en-2-yl]isoquinoline. Cyclization of the diketones is effected conveniently with sulfuric acid to afford the corresponding dl-2-aza-3-substituted-11β-methylestra-1,3,5(10),8(14),9(11),15-hexaen17-ones. Representative thereof is the formation of dl-2-aza-3-methoxy-11α-methylestra-1,3,5-(10), 8(14), 9(11), 15-hexaen-17-one upon contacting the aforementioned isoquinoline derivative with sulfuric acid.

Reduction of the 17-ketone moiety with a metallic hydride reducing agent, as for example, diisobutyl aluminum hydride, affords the 17β-ol. Catalytic hydrogenation, using a palladium-on-calcium carbonate catalyst effects saturation of the 15-double bond. Further catalytic reduction utilizing palladium-on-alumina affords those derivatives having the 1,3,5(10), and 8-double bonds. Typically dl-2-aza-3-methoxy-11β-methylestra-1,3,5(10),8(14),9(11),15-hexaen-17-one is reduced with diisobutylaluminum hydride to the 17β-ol corresponding, and then subsequent hydrogenation as described above yields dl-2-aza-3-methoxy-11β-methylestra-1,3,5(10),8-tetraen-17β-ol. Reduction of the 8-double bond then can be accomplished with sodium metal in liquid ammonia to produce the instant compounds, e.g. dl-2-aza-3-methoxy-11β-methylestra-1,3,5(10)-trien-17β-ol. A particularly preferred method of producing the instant compounds is to treat the tetraenes with sodium metal in liquid ammonia to produce the corresponding dl-2-aza-11β-alkyl-3-substituted estra-2,5(10)-dien-17β-ols, which then are rearomatized with dichlorodicyanobenzoquinone to yield the desired dl-2-aza-11β-alkyl-3-substituted-estra-1,3,5(10)-trien-17β-ols. Acylation of the 17β-ol derivatives, e.g. with the appropriate acid anhydride in pyridine, affords the 17β-alkanoyl derivatives.

Subsequent oxidation of the 17β-ols with sulfur trioxide in pyridine or with chromic acid yields the 17-ketones, e.g. dl-2-aza-3-methoxy-11-methylestra-1,3,5(10)-trien-17-one.

The 2-azaestratrienes, as typified by dl-2-aza-3-methoxyestra-1,3,5(10)-trien-17β-ol, are valuable pharmacological agents as is evidenced by their anti-viral activity. A suitable assay for detection of that activity is described as follows:

Cell cultures of primary Rhesus monkey kidney maintained in 25 cc. plastic flasks and each containing test compound in concentrations of 625, 125, 25, 5 or 1 μg./ml. are prepared in pairs. These flasks and an identical pair of flasks containing no test compound are each inoculated with a dose of influenza virus type A (Strain 575) previously shown to produce maximum hemadsorption and minimum cytopathogenic effects after a 24-hour incubation. Where the cultures contain test compound the viruses are added 1 hour after addition of the test compound to the culture. After 24 hour incubation of the cultures the supernatant fluids are removed and 3.0 ml. of a 0.4% suspension of guinea pig erythrocytes is added to each flask. The flasks are then incubated at 4° C. in a horizontal position for 30 minutes. The flasks are rocked every 10 minutes during the incubation period. After this incubation the red cell suspension is decanted from each flask. The flasks are washed twice with 3.0 ml. of phosphate buffer solution (pH 7.4) to remove unabsorbed red cells and 3.0 ml. of distilled water is then added to lyse the absorbed cells. The flasks are then further incubated at 37° C. for 30 minutes in a horizontal position and the flasks are rocked every 10 minutes. After this incubation the fluid contents of the pairs of flasks are combined to form an assay unit and are placed at room temperature for 15–30 minutes to allow settling of the cellular debris. A pair of control flasks identical with the above except for the absence of the test compound and virus inoculation are run concurrently. The resulting hemoglobin solutions from each assay unit are then read for optical density in a Beckman spectrophotometer at about 415 mμ. A test compound is considered active if at any one of the tested levels it reduces the optical density reading by at least 50% relative to the virus control.

Even though the above test procedure describes in detail and in vitro use for the 2-azaestratrienes and more particularly for dl-2-aza-3-methoxyestra-1,3,5(10)-trien-17β-ol, it is not to be construed from such a disclosure that the instant compounds are limited to an in vitro use but that, in fact, such an in vitro disclosure of use would teach to a person skilled in virology arts how to use the instant compounds in vivo. Thus, the in vitro concentration range of 5–625 micrograms per milliliter provides a basis upon which those skilled in the art can use the compounds in vivo. For example amantadine (Symmetrel ®) is a therapeutic antiviral agent against influenza $A_2$, (*Cuttings Handbook of Pharmacology* 4th Ed., Appleton-Century-Crafts, N.Y. 1969 (Chapt. 19). It is active in the present test and therapeutically active in vivo at 200 mg. per day.

The hypolipidemic properties of the instant compounds is illustrated in the following assay:

Male Charles River rats (160–200 g.), having had free access to food and water, are administered a standard diet containing 2% DEAE - cellulose (Reeve Angel anion exchange resin) for 5 days. The rats then are sacrificed and their livers removed immediately. The livers are homogenized in a medium consisting of 0.1 M potassium phosphate, pH 7.4, 0.004 m $MgCl_2$ and 0.03 M nicotinamide, and the microsomal-cytosol fraction obtained by centrifugation. 2.0 ml. of the microsomal-cytosol fraction is incubated, at 37° C. for 90 minutes for measurement of cholosterol biosynthesis, in a standard assay mixture containing 10 micromoles of $C^{14}$-labeled mevalonic acid, 2 micromoles nicotinamide adenine dinucleotide, 2 micromoles nicotinamide adenine dinucleotide phosphate, and 20 micromoles glucose-6-phosphate, and test compound, initially at 0.001 M, is added. All assays are run in duplicate with the assay to which no test compound is added serving as a control. Heat inactivated homogenate serves as blank for both control and test systems.

Reaction rate is determined per unit of time by the amount of $C^{14}$-label incorporated into the lipid fraction from the radioactive mevalonic acid. Results are reported as % inhibition (i.e. (Reaction Rate for Test Compound/Reaction Rate for Control) × 100).

Compounds of the present invention can also be converted into useful anti-inflammatory compounds by the following reaction sequence.

7-Aza-6-methoxy-1-tetralone is reacted with glyoxylic acid to provide 7-aza-2-carboxy-hydroxymethyl-6-methoxy-1-tetralone and this compound is dehydrated by heating in base to provide 7-aza-2-carboxy-methylidene-6-methoxy-1-tetralone. Saturation of the double bond with zinc in acetic acid followed by acid catalysed esterification with methanol and sulfuric acid provides 7-aza-6-methoxy-2-methoxycarbonylmethyl-1-tetralone. 7-Aza-6-methoxy-2-methoxycarbonylmethyl-1-tetralone to methyl 8-hydroxy-3-methoxy-5,6,7,8-tetrahydro-2-azanaphthalene-7-acetate by reaction with sodium borohydride and reaction of this product with Pd on Carbon/anisole provides methyl-3-methoxy-2-azanaphthalene-7-acetate which is alkylated with methyl iodide and base to provide methyl 3-methoxy-2-azanaphthalene-7-α-methyl-acetate and hydrolysis of this ester provides 3-methoxy-2-azanaphthalene-7-α-methylacetic acid.

An alternate procedure to the above-described reaction sequence is as follows: The 7-aza-6-methoxy-carboxymethylidene-1-tetralone is acid catalysed with methanol to give the corresponding ester. This resulting ester is reduced to 8-hydroxy-3-methoxy-5,6,7,8-tetrahydro-7-methoxy-carbonylmethylidene-2-azanaphthalene which in turn is reacted with 2-equivalents of lithium diisopropylamine in tetrahydrofuran at −78° C.

Following hydrolysis and acetic acid catalyzed dehydration of the resultant allylic alcohol to the azanaphthalene derivative, further treatment with lithium diisopropylamine, followed by alkylation with methyl iodide provides methyl 3-methoxy-2-azanaphthalene-7-α-methylacetate which is hydrolysed to 3-methoxy-2-azanaphthalene-7-α-methyl acetic acid. This acid is conveniently resolved into the d and l optical isomers by mixing a hot solution of 7.15 parts of the above acid in 20 parts by volume of methanol and 5 parts by volume of acetone and 1.5 parts of cinchonidine in 15 parts by volume of methanol and 10 parts by volume of acetone and then cooling the resulting solution. A salt precipitates upon cooling and this salt is filtered and crystallized from methanol-acetone and the free acid is liberated from the salt by shaking with a mixture of dilute hydrochloric acid and benzene. Evaporation of the benzene layer and crystallization of the residue from acetone-hexane provides d-α-methyl-2-azanaphthalene-7-α-methylacetic acid, the d enantiomer. Acidification of the mother liquor from the cinchonidine salt solution provides the l-enantiomer, l-3-methoxy-2-azanaphthalene-7-α-methylacetic acid.

The corresponding aldehydes and alcohols of l-3-methoxy-2-azanaphthalene-7-α-methylacetic acid are potent anti-inflammatory compounds.

Anti-inflammatory utility of these aldehydes and alcohols is shown by the results of a standardized test for their capacity to inhibit the edema induced in rats by injection of *Mycobacterium butyricum*. The procedure, which is similar to one described by Pearson et al. in Arthritis Rheumat., 2, 440 (1959), follows. Intact male Sprague-Dawley rats (60–70 grams) are randomized in groups of 12, one group for each compound to be tested plus one group to serve as controls. Each animal is injected intradermally (without any anesthesia) on the base of the tail with 0.6 mg. of dry heat-killed *Mycobacterium butyricum* (difco 0640-33) suspended in 0.05 ml. of paraffin oil containing 2% digitonin whereupon the prescribed dose of compound, initially 10 mg/kg per day, dissolved or suspended in a vehicle consisting of 0.2 ml. of either corn oil or a mixture of 20 ml of aqueous 0.85 sodium chloride with 1 drop of polysorbate 80, is intragastrically or subcutaneously administered. Administration thus of compound is repeated daily for the next 18 consecutive days. The control group is identically and concurrently administered vehicle alone. On the 20th day, the rats are sacrificed and the total volume of each pair of hind feet is measured in arbitrary units. A compound is considered anti-inflammatory if the average volume (T) of the hind feet in the group treated therewith is significantly ($P = 0.05$) less than the corresponding value (C) for the control group. Hydrocortisone administered intragastrically has an $ED_{50}$ of approximately 7.0 mg/kg/day in this test. Dl 3-methoxy-2-azanaphthalene-7-α-methylacetic acid has an $ED_{50}$ of about 5.0 mg/kg/day in the above test.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are given in degrees centigrade (° C.) and relative amounts of materials in parts by weight, except as otherwise noted.

EXAMPLE 1

To a solution of 400 parts of dihydroresorcinol in 2000 parts by volume of chloroform is added 161.2 parts of phosphorus trichloride and the resulting reaction mixture is stirred and heated at reflux temperature in a nitrogen atmosphere for about 3.5 hours. The mixture is then cooled and poured carefully into approximately 1000 parts of a mixture of ice and water. The layers are separated and the aqueous phase is extracted with ether. The ether extracts are combined with the chloroform layer and the resulting organic solution is washed successively with 5% aqueous sodium hydroxide and water, then dried over anhydrous sodium sulfate. Removal of the solvent by distillation under reduced pressure affords the crude product, which is purified by distillation under reduced pressure, thus affording 3-chloro-2-cyclohexen-1-one, boiling at about 65° under 3 mm. pressure.

EXAMPLE 2

To a mixture of 58 parts of sodium hydride an 1800 parts by volume of ethylene glycol dimethyl ether, under nitrogen, is added, at room temperature over a period of about 30 minutes, 198 parts of cyanoacetamide. That mixture is heated at the reflux temperature for about 30 minutes, then cooled to approximately room temperature and 145.2 parts of 3-chloro-2-cyclohexen-1-one is added over a period of about 15 minutes. The mixture is stirred and heated at the reflux temperature for about 1 hour, then is cooled and a solution consisting of 20 parts by volume of methanol and 10 parts by volume of water is cautiously added dropwise. An additional 500 parts of water is then added and the organic solvents are removed by distillation under reduced pressure. Acidification of the residual aqueous solution to pH 1–2 results in precipitation of the product, which is isolated by filtration, then washed with cold water and dried. Purification of that crude product is effected by recrystallization from ethanol-water-ethyl acetate, thus affording α-cyano-3-oxo-1-cyclohexen-1-acetamide, melting at about 181°–183°, and is represented by the following structural formula.

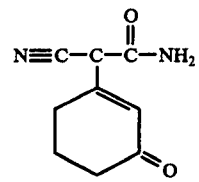

EXAMPLE 3

To a solution consisting of 40 parts of α-cyano-3-oxo-1-cyclohexen-1-acetamide in 125 parts by volume of dimethylformamide, in an atmosphere of nitrogen, is added dropwise, over a period of 10–15 minutes, 40 parts of dimethylformamide diethyl acetal. After the reaction mixture is stirred at room temperature for about 18 hours, 10 parts of water is added and the organic solvents are removed by distillation under reduced pressure. The residual oily product is extracted with dilute aqueous sodium hydroxide and the extract is washed several times with chloroform, then filtered to remove the small amount of insoluble material. Neutralization of the alkaline solution by the addition of dilute hydrochloric acid results in precipitation of the product, which is purified by recrystallization from aqueous acetone to afford 2,3,5,6,7,8-hexahydro-3,8-dioxo-4-isoquinolinecarbonitrile, melting above 290°.

EXAMPLE 3B 75 parts of α-cyano-3-oxo-1-cyclohexen-1-acetamide in 400 parts by volume of dimethylformamide and 75 parts of triethyl orthoformate are heated on a steam bath for 3 hours to 16 hours. Solvent was then removed in vacuum to give a syrup which is taken up in ethyl acetate. Cooling of this solution gives 2,3,5,6,7,8-hexahydro-3,8-dioxo-4-isoquinolinecarbonitrile which is identical to the product of Example 3.

EXAMPLE 4

A solution of 28.4 parts of 2,3,5,6,7,8-hexahydro-3,8-dioxo-4-isoquinolinecarbonitrile in 500 parts by volume of 48% hydrobromic acid is heated at the reflux temperature in the absence of light for about 7 hours, following which time the solvent is removed by distillation under reduced pressure. The resulting residue is partitioned between chloroform and aqueous sodium chloride and the layers are separated. The aqueous phase is extracted several times with chloroform, then combined with the original chloroform layer. That organic solution is washed with aqueous sodium chloride, then dried over anhydrous sodium sulfate and stripped of solvent under reduced pressure to afford the crude product. The original aqueous layer is neutralized by the addition of sodium bicarbonate, then is extracted with chloroform. Evaporation of that chloroform extract to dryness affords additional product. The combined crude product is purified by recrystallization from aqueous acetone, thus affording 2,3,5,6,7,8-hexahydro-3,8-isoquinolinedione, melting at about 246°-248° with decomposition.

EXAMPLE 5

To a solution of 2.6 parts of 2,3,5,6,7,8-hexahydro-3,8-isoquinolinedione in 375 parts by volume of dry benzene is added 2.3 parts of silver carbonate and 5 parts by volume of methyl iodide and the resulting mixture is heated at the reflux temperature in the absence of light under an atmosphere of nitrogen for about 4 hours. At the end of that time the mixture is cooled and filtered through diatomaceous earth to afford an organic solution, which is extracted several times with 6 N hydrochloric acid. Those acidic extracts are washed with chloroform, then made alkaline by the addition of aqueous sodium hydroxide and extracted with ether. The ether extracts are combined and washed with saturated aqueous sodium chloride, then dried over anhydrous sodium sulfate and stripped of solvent under reduced pressure. The resulting crude product is purified by recrystallization from water to yield 7-aza-6-methoxy-1-tetralone, melting at about 55.5°-57° and represented by the following structural formula.

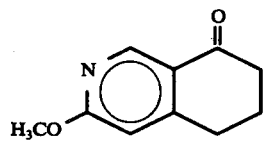

The aforementioned chloroform washings are evaporated to dryness under reduced pressure and the residual oil is extracted with benzene. The resulting organic solution is diluted with hexane to the point of incipient turbidity, then is decolorized with activated carbon. The decolorized solution is diluted with hexane, then cooled, thus affording crystalline 2-methyl-2,3,5,6,7,8-hexahydro-3,8-isoquinolinedione, melting at about 94°-97° C.

EXAMPLE 6

To a solution of 10 parts of 7-aza-6-methoxy-1-tetralone in 140 parts by volume of xylene, in a nitrogen atmosphere, is added dropwise, at −20° C. over a period of about 45 minutes, 45 parts by volume of 2.84 M vinyl magnesium chloride in tetrahydrofuran dissolved in 60 parts by volume of xylene. The resulting reaction mixture is stirred between −15° and −20° C. for about 90 minutes, then is diluted with approximately 100 parts by volume of saturated aqueous ammonium chloride. That diluted mixture is allowed to warm to room temperature, at which time the layers are separated and the aqueous phase is extracted with ether. The combined organic extracts are washed successively with aqueous ammonium chloride and saturated aqueous sodium chloride, then dried over anhydrous sodium sulfate. To that organic solution containing 7-aza-6-methoxy-1-vinyl-1-tetralol is added 6.9 parts of 2-methylcyclopentane-1,3-dione and 5.8 parts of triethylamine and that reaction mixture is partially concentrated to remove the ether and tetrahydrofuran, then is heated at the reflux temperature under nitrogen, during which time the water of reaction is removed by means of a water trap. That mixture is then cooled and extracted with dilute aqueous sodium hydroxide. The layers are separated and the aqueous layer is extracted with benzene. The organic solutions are combined, washed with saturated aqueous sodium chloride, dried over anhydrous sodium sulfate, decolorized with activated carbon, then filtered. Removal of the solvent by distillation under reduced pressure affords an oily residue, which is purified by crystallization from ether, thus affording 5,6,7,8-tetrahydro-3-methoxy-8-[(2-methyl-1,3-dioxocyclopent-2-yl)ethylidene]isoquinoline, melting at about 79°-80.5° C.

EXAMPLE 7

To a solution of 15 parts of p-toluenesulfonic acid monohydrate in 750 parts by volume of dioxane is added a solution of 8.75 parts of 5,6,7,8-tetrahydro-3-methoxy-8-[(2-methyl-1,3-dioxocyclopent-2-yl)ethyliden]isoquinoline in 1500 parts by volume of xylene and the resulting reaction mixture is heated at reflux temperature under nitrogen for about 3 hours. That mixture is then cooled and 200 parts by volume of dilute aqueous sodium bicarbonate is added. The organic layer is separated and washed several times with saturated aqueous sodium chloride, then dried over anhydrous sodium sulfate and stripped of solvent by distillation under reduced pressure. The resulting deep red oily residue is triturated with acetone to yield the desired product. Further purification is effected by recrystallization from acetone, thus affording dl-2-aza-3-methoxyestra-1,3,5(10),8,14-pentaen-17-one, melting at about 167°-169° C. with decomposition.

EXAMPLE 8

To a solution of 3.75 parts of dl-2-aza-3-methoxyestra-1,3,5(10),8,14-pentaen-17-one, in 125 parts by volume of methanol is added portionwise at room temperature 1.4 parts of sodium borohydride. After completion of the addition, the reaction mixture is stirred for several minutes, then is quenched by the addition of acetone. Concentration of the solution to approximately one-half volume is followed by the addition of a small amount of water and cooling, thus effecting precipitation of yellow plate-like crystals. That crude product is purified by recrystallization from aqueous acetone to yield dl-2-aza-3-methoxyestra-1,3,5(10),8,14-pentaen-17β-ol, melting at about 130°–136° C.

EXAMPLE 9

A mixture consisting of 0.68 part of dl-2-aza-3-methoxyestra-1,3,5(10),8,14-pentaen-17-one, 100 parts by volume of benzene and 0.14 part of 5% palladium-on-calcium carbonate catalyst is stirred in a hydrogen atmosphere at room temperature and atmospheric pressure until one molecular equivalent of hydrogen has been absorbed. The reaction mixture is then filtered to remove the catalyst and the filtrate is concentration to dryness to afford the crude product. Recrystallization of that material from methanol affords pure dl-2-aza-3-methoxyestra-1,3,5(10),8-tetraen-17-one, melting at about 146°–149.5° C.

EXAMPLE 10

To a solution of 3.85 parts of dl-2-aza-3-methoxyestra-1,3,5(10),8,14-pentaen-17β-ol in 150 parts by volume of benzene is added 1.5 parts of 5% palladium-on-calcium carbonate catalyst and that mixture is shaken with hydrogen until one molecular equivalent of hydrogen has been absorbed. Removal of the catalyst by filtration followed by partial concentration of the filtrate and cooling results in crystallization of the product, which is isolated by filtration to afford dl-2-aza-3-methoxyestra-1,3,5(10),8,pentaen-17β-ol, melting at about 155°–157° C.

EXAMPLE 11

A solution of 0.4 part of dl-2-aza-3-methoxyestra-1,3,5(10),8-tetraen-17β-ol in 25 parts by volume of tetrahydrofuran is added to approximately 40 parts by volume of ammonia, at about −70° in an atmosphere of nitrogen. To that mixture is then added 0.4 part of sodium metal and the resulting mixture is stirred for about 1 hour, at the end of which time an additional 0.15 part of sodium metal is added. Stirring is continued for approximately 45 minutes, at the end of which time approximately 4 parts of ammonium chloride is added and the mixture is allowed to warm to room temperature. Extraction with ether affords an organic solution, which is stripped of solvent under reduced pressure to afford an oily residue, consisting of a mixture of dl-2-aza-3-methoxyestra-1,3,5(10)-trien-17β-ol and dl-2-aza-3-methoxyestra-2,5(10)-dien-17β-ol. That residue is dissolved in a mixture consisting of 20 parts by volume of benzene and 10 parts by volume of acetone and the solution is cooled to approximately −10° at which time 0.32 part of dichlorodicyanobenzoquinone is added portionwise. The mixture is allowed to warm to about 10° for about 40 minutes and 10% aqueous sodium bisulfite is then added. The mixture is stirred, the layers separated and the aqueous phase extracted with ether. The combined ether extracts are washed several times with dilute aqueous sodium hydroxide, then with aqueous sodium chloride. After drying of that solution over anhydrous sodium sulfate, the solution is diluted with hexane, then filtered through diatomaceous earth. Removal of the solvent under reduced pressure affords an oil, which is triturated with methanol to yield the crude product. Recrystallization from methanol affords dl-2-aza-3-methoxyestra-1,3,5(10)-trien-17β-ol, melting at about 153°–156° C.

EXAMPLE 12

The substitution of an equivalent quantity of ethyl iodide in the procedure of Example 5 results in 7-aza-6-ethoxy-1-tetralone, which when substituted in the subsequent procedures described in Examples 6–11 affords 7-aza-6-ethoxy-1-vinyl-1-tetralol; 5,6,7,8-tetrahydro-3-ethoxy-8-[(2-methyl-1,3-dioxycyclopent-2-yl)ethylidene]isoquinoline; dl-2-aza-3-ethoxyestra-1,3,5(10),8,14-pentaen-17-one; dl-2aza-3-ethoxyestra-1,3,5(10),8,14-pentaen-17β-ol; dl-2-aza-3-ethoxyestra-1,3,5(10),8-tetraen-17-one; dl-2-aza-3-ethoxyestra-1,3,5(10),8-tetraen-17β-ol; and dl-2-aza-3-ethoxyestra-1,3,5(10)-trien-17β-ol.

EXAMPLE 13

To a solution of 1 part of 7-aza-6-methoxy-1-vinyl-1-tetralol in 20 parts by volume of acetic acid is added 0.4 part of thiourea and the resulting reaction mixture is warmed to achieve homogeneity. Removal of the solvent by distillation under reduced pressure affords 5,6,7,8-tetrahydro-3-methoxyisoquinolin-8-ethylidenisothiouronium acetate.

To a solution containing 1 part of 5,6,7,8-tetrahydro-3-methoxyisoquinolin-8-ethylidenisothiouronium acetate in 20 parts by volume of 50% aqueous ethanol is added a solution of 0.5 part of 2-methylcyclopentane-1,3-dione in 5 parts of ethanol and that mixture is heated at the reflux temperature for about 1 hours, then cooled and diluted with water to effect precipitation of the product, which is isolated by filtration and dried, thus affording 5,6,7,8-tetrahydro-3-methyoxy-8-[(2-methyl-1,3-dioxocyclopent-2-yl)ethyliden]isoquinoline, identical with the product of Example 6.

EXAMPLE 14

To 50 parts by volume of liquid ammonia, at about −78° in a nitrogen atmosphere, is added successively 30 parts by volume of tetrahydrofuran and sufficient sodium metal to produce a blue color in the solution. At that time an additional 0.4 part of sodium metal is added, the mixture is stirred for about 15 minutes and 0.48 part of dl-2-aza-3-methoxyestra-1,3,5(10),8-tetraen-17β-ol dissolved in 10 parts by volume of tetrahydrofuran is added. Stirring at approximately −78° is continued for about 45 minutes and the reaction mixture is then quenched by the addition of sufficient wet ether to discharge the blue color. Most of the ammonia is allowed to evaporate and the residual mixture is diluted with ether, then filtered to remove inorganic salts. The filtrate is partially concentrated, diluted with benzene, filtered through diatomaceous earth and stripped of solvent to afford a yellow oil consisting of a mixture of dl-2-aza-3-methoxyestra-1,3,5(10)-trien-17β-ol and dl-2-aza-3-methoxyestra-2,4-dien-17β-ol. Fractional crystallization of that oil from methanol affords dl-2-aza-3-methoxyestra-2,4-dien-17β-ol, melting with decomposition at about 172°–176° C. The mother liquors are concentrated to dryness and the residue reacted with dichlorodicyanobenzoquinone according to the procedure of Example 11, thus affording dl-2-aza-3-methoxyestra-1,3,5(10)-trien-17β-ol, identical with the product of that of Example 11.

EXAMPLE 15

To 43 parts of 2-bromo-3-dimethylaminopropene in 650 parts of toluene, cooled to about −10° under an atmosphere of nitrogen, is added 130 parts by volume of 2.04 N butyl lithium in hexane solution at a rate so as to maintain a temperature below −5° during the addition. After stirring for about 10 minutes, 9.8 parts of 7-aza-6-methoxy-1-tetralone, dissolved in 22 parts of benzene, is added over a 10 minute period and the cooling bath is removed. After about 20 minutes when the temperature of the reaction mixture has reached approximately 5°, the reaction mixture is quenched by the addition of 150 parts by volume of a saturated ammonium chloride solution. The two phases which form are separated and the aqueous solution is extracted with benzene. The combined extracts are subsequently extracted themselves with 5 portions of 5% aqueous formic acid solution. The acidic extracts are backwashed once with benzene before neutralization to pH 7 with aqueous ammonia and extraction with chloroform. Then the extracts are washed with a saturated sodium chloride solution and dried over anhydrous sodium sulfate. Upon solvent removal, crude product is obtained as an oil. The oil is dissolved into ether, and n-hexane is added until the solution becomes turbid. The solution then is filtered through diatomaceous earth and pure N,N-dimethyl-N-(2-[5,6,7,8-tetrahydro-8-hydroxy-3-methoxyisoquinol-8-yl]prop-2-en-1-yl)amine is obtained upon reducing the volume of the solution and allowing the mixture to stand at room temperature. That material melts at about 66°–68° C.

EXAMPLE 16A

To 7.1 parts of N,N-dimethyl-N-(2-[5,6,7,8-tetrahydro-8-hydroxy-3-methoxyisoquinol-8-yl]prop-2-en-1-yl)amine in 31 parts of benzene and 34.5 parts of pyridine is added 4.5 parts of phosphorous oxychloride, dropwise and at room temperature. That solution is stirred at room temperature for several hours, then cooled in an ice bath. 25 Parts of water is added slowly followed by enough 5% aqueous sodium hydroxide solution to bring the pH of the solution to about 10. Ether is added and the organic and aqueous layers separated. The aqueous layer is extracted with ether and the extracts washed with saturated sodium chloride and dried over anhydrous sodium sulfate. Approximately 200 parts of n-hexane is added to the solution, followed by a portion of charcoal. That mixture is filtered through diatomaceous earth to give a light yellow solution which, upon solvent removal, affords a yellow oil yielding upon crystallization N,N-dimethyl-N-(2-[5,6-dihydro-3-methoxyisoquinol-8-yl]prop-2-en-1-yl)amine. A portion of that material is distilled and the distillate is taken up into methanol-water and upon standing yields crystals melting at about 42°–45° C.

EXAMPLE 16B

A solution of 0.04 part of N,N-dimethyl-N-(2-[5,6,7,8-tetrahydro-8-hydroxy-3-methoxyisoquinol-8-yl]prop-2-en-1-yl)amine and 0.5 part by volume of concentrated sulfuric acid is allowed to stand at room temperature for about 30 minutes. Then the reaction mixture is added to water and basified with aqueous ammonia. The solution is extracted with ether and the ethereal extracts are washed with saturated sodium chloride solution, dried over anhydrous sodium sulfate and evaporated under reduced pressure to yield N,N-dimethyl-N-(2-[5,6-dihydro-3-methoxyisoquinol-8-yl]prop-2-en-1-yl)amine, identical to the product of Example 16A.

EXAMPLE 17

To a solution containing 4.3 parts of N,N-dimethyl-N-(2-[5,6-dihydro-3-methoxyisoquinol-8-yl]prop-2-en-1-yl)amine in 88 parts of benzene is added 10 parts by volume of methyl iodide, and the mixture is allowed to stand at room temperature for 3½ hours. The precipitate which forms then is filtered, washed with additional benzene, and dried affording crude product which, upon recrystallization from acetone-ethylacetate, gives pure N,N,N-trimethyl-N-(2-[5,6-dihydro-3-methoxyisoquinol-8-yl]prop-2-en-1-yl)ammonium melting at about 165°–169° C.

EXAMPLE 18A 5.8 Parts of N,N,N-trimethyl-N-(2-[5,6-dihydro-3-methoxyisoquinol-8-yl]prop-2-en-1-yl)ammonium iodide is dissolved in a mixture of 64 parts of methanol and 20 parts of water, then treated with 1.9 parts of silver oxide. The solution is stirred in the absence of light for 1 hour, then filtered through diatomaceous earth. The filtrate is treated with 2.0 parts of 2-methylcyclopentane-1,3-dione, and the solvent is removed under reduced pressure at about 50°. The oily residue which remains is taken up into 26 parts of dioxane, and 132 parts of xylene is added, followed by 4 parts by volume of triethylamine. The solution is heated to reflux temperature and refluxed overnight under a nitrogen atmosphere, then 5% aqueous sodium hydroxide solution is added. The layers are separated and the organic phase is washed with saturated sodium chloride and extracted with 2.5% aqueous formic acid. The acidic extracts are backwashed with benzene and combined. After washing with saturated sodium chlorine solution, drying over anhydrous sodium sulfate and removing solvent, an oil remains which crystallizes upon scratching to afford crude product. Pure 5,6-dihydro-3-methoxy-8-[3-(2-methyl-1,3-dioxocyclopent-2-yl)prop-1-en-2-yl]isoquinoline is obtained upon recrystallization from acetone. That material is characterized by maxima in the ultraviolet spectrum in methanol at 261 millimicrons with a molecular extinction coefficient at about 12,200, and maximum in the nuclear magnetic resonance spectrum in deuteriochloroform at 64, 156, 265, 237, 306, 345, 395 and 470.

EXAMPLE 18B

A solution containing 0.75 part of 2-methylcyclopentane-1,3-dione in 19 parts of dimethylformamide is treated sequentially with 1.0 part by volume of triethylamine and 1.9 parts of N,N,N-trimethyl-N-(2-[5,6-dihydro-3-methoxyisoquinol-8-yl]prop-2-en-1-yl)ammonium iodide. The resulting homogeneous solution is heated at about 135° for 4¾ hours. It is allowed to cool to room temperature and solvent is removed under reduced pressure. The remaining material is diluted with water-ether and enough 5% sodium hydroxide solution is added to bring the pH to 10. The aqueous and organic layers are separated and the aqueous layer is extracted with ether. The extracts are washed sequentially with 5% sodium hydroxide solution, 2.5% aqueous formic acid and saturated sodium chloride solution, then dried over anhydrous sodium sulfate. Upon solvent removal, an oil remains which is taken into ether. Then n-hexane is added until the solution becomes turbid. Charcoal is added and the mixture is filtered. Solvent is removed under reduced pressure to yield an oil which crystallizes upon standing. Recrystallization from acetone-water gives pure 5,6-dihydro-3-methoxy-8-[3-(2-methyl-1,3-dioxocyclopent-2-yl)prop-1-en-2-yl]isoquinoline, which is identical to the product obtained in Example 18A.

EXAMPLE 19

To 40 parts by volume of concentrated sulfuric acid, cooled to about −5° with a cooling bath, is added 2.4 parts of 5,6-dihydro-3-methoxy-8-[3-(2-methyl-1,3-dioxocyclopent-2-yl)prop-1-en-2-yl]isoquinoline, portionwise at a rate such that the temperature does not exceed 10°. After the additions are completed, the cooling bath is removed and the solution allowed to warm to room temperature over approximately a 20 minute period. The solution then is added to 100 parts of water, cooled in an ice bath, and basified with ammonium hydroxide to afford a precipitate, which is recovered by filtration. That material is recrystallized from acetone to give pure compound, dl-2-aza-3-methoxy-11β-methylestra-1,3,5(10),8(14),9(11),15-hexaen-17-one, melting at about 197°–198.5° C.

EXAMPLE 20

A solution of 2.1 parts of dl-2-aza-3-methoxy-11β-methylestra-1,3,5(10),8(14),9(11),15-hexaen-17-one in 66 parts of benzene and 36 parts of ethyl ether, cooled to 0°, is treated with 12 parts of a 20% diisobutyl aluminum hydride in toluene solution. The reducing agent is added dropwise over a 10 minute period. The initially heterogeneous solution becomes homogeneous and is stirred for about 15 minutes before destroying reducing agent with isopropyl alcohol. Water, acidified with a small quantity of hydrochloric acid, is added to form 2 layers. The slightly acidic aqueous layer is extracted with benzene and the pH of the aqueous solution then is adjusted to approximately 6.5 to 7 with ammonium hydroxide. The aqueous layer is extracted with chloroform. The extracts are combined and upon solvent removal an oil remains which is triturated with methanol to give crude crystalline product. Pure dl-2-aza-3-methoxy-11β-methylestra-1,3,5(10),8(14),9(11),15-hexaen-17β-ol, melting at about 95°–100°, is obtained upon recrystallization from methanol.

EXAMPLE 21

A mixture consisting of 1.0 part of dl-2-aza-3-methoxy-11β-methylestra-1,3,5(10),8(14),9(11),15-hexaen-17β-ol, 200 parts by volume of benzene, and 0.5 part of 5% palladium-on-calcium carbonate catalyst is stirred in a hydrogen atmosphere at room temperature and atmospheric pressure until approximately a molecular equivalent of hydrogen has been absorbed. The solvent is removed under reduced pressure to yield an oil which is taken up into denatured ethanol. Upon cooling, dl-2-aza-3-methoxy-11β-methylestra-1,3,5(10),8(14),9(11)-pentaen-17β-ol forms as yellow crystals. That material exhibits maxima in the ultraviolet spectrum in methanol at about 291 millimicrons with a molecular extinction coefficient of about 6860, 242 millimicrons with a molecular extinction coefficient of about 21,900 and 247 millimicrons with a molecular extinction coefficient of about 20,900. It further is characterized by maxima in the nuclear magnetic resonance spectrum in deuterio chloroform at about 55, 122, 135, 237, 243 and 488 Hertz.

EXAMPLE 22

To a solution of 3.7 parts of dl-2-aza-3-methoxy-11β-methylestra-1,3,5(10),8(14),9(11)-pentaen-17β-ol in 79 parts of ethanol is added 1.8 parts of 5% palladium-on-alumina catalyst and that mixture is shaken with hydrogen until a molecular equivalent of hydrogen has been absorbed. The catalyst is removed by filtration and the solvent removed under reduced pressure to give an oil, which when taken up in methanol and cooled yields crystalline dl-2-aza-3-methoxy-11β-methylestra-1,3,5(10),8-tetraen-17β-ol, melting at about 164°–167.5° C.

EXAMPLE 23

To 50 parts by volume of freshly distilled ammonia, cooled to −78° under a nitrogen atmosphere, is added 0.55 part of sodium metal in small pieces. The mixture is stirred for approximately 15–30 minutes, then 0.30 part of dl-2-aza-3-methoxy-11β-methylestra-1,3,5(10),8-tetraen-17β-ol in 18 parts of tetrahydrofuran is added to the deep blue solution over a 5 minute period. The reaction mixture is stirred at −78° for about 30 minutes, then 2.0 parts of ammonium chloride is added. The cooling bath is removed and the reaction mixture is allowed to warm to about −33° at which point the ammonia is distilled off. A portion of ether is added as the ammonia evaporates and after evaporation, saturated sodium chloride solution is added, and the ether layer is separated from the aqueous phase. The organic phase is washed with additional sodium chloride solution and dried over anhydrous sodium sulfate. Upon solvent removal, desired product and crude dl-2-aza-3-methoxy-11β-methylestra-2,4(10)dien-17β-ol remains as an oil. The crude oil is taken up in a mixture of 5 parts by volume of acetone and 5 parts by volume of benzene, and to this solution is added 0.250 part of dichlorodicyanobenzoquinone. The reaction mixture is stirred at room temperature for about 15 minutes, after which time 25 parts by volume of a 10% sodium bisulfite solution and a portion of ether is added. The two layers are separated and the organic phase is washed with 5% sodium hydroxide solution and saturated sodium chloride solution and dried over anhydrous sodium sulfate. The dried solution is treated with activated charcoal and filtered through diatomaceous earth. Solvent removal gives an oil which, upon crystallization from methanol and recrystallization from ether-methanol, gives pure dl-2-aza-3-methoxy-11β-methylestra-1,3,5(10)-trien-17β-ol, melting at about 168°–169° C.

EXAMPLE 24

0.100 Part of dl-2-aza-3-methoxy-11β-methylestra-1,3,5(10)-trien-17β-ol in 1 part by volume of dimethylsulfoxide containing 0.25 part by volume of triethylamine is stirred vigorously, then treated with 0.15 part of sulfur trioxide-pyridine salt. The reaction mixture is stirred for 20 minutes to afford an oil, which upon continued stirring becomes a red solid. The solid is recovered and recrystallized from methanol to give dl-2-aza-3-methoxy-11β-methylestra-1,3,5(10)-trien-17-one, melting at about 155°–160° C.

EXAMPLE 25

To 5 parts of 7-aza-6-methoxy-1-tetralone in 50 parts by volume of methanol is added 3.0 parts of glyoxylic acid hydrate followed by 30 parts by volume of 5% aqueous sodium hydroxide and the reaction mixture is stirred at room temperature for 4 hours. Sufficient acetic acid is added to lower the pH of the solution to about 5. The solution is then extracted 6 times with ethyl acetate. The combined extracts are filtered and dried over anhydrous sodium sulfate. Removal of the solvent provides 7-aza-2-carboxyhydroxymethyl-6-methoxy-1-tetralone, melting at 165°–166° C. Continued heating on a steam bath for 2.5 hours followed by isolation of the acid provides 7-aza-6-methoxy-2-carboxymethylidene-1-tetralone melting at 221°–222° C.

0.5 Part of this compound in 16 parts by volume of acetic acid, 8 parts by volume of water and 0.3 part of zinc dust is refluxed for 0.5 hour. The solution is cooled and the zinc is filtered. The volume of the filtrate is reduced to 10–15 parts by volume and to this concentrate is added 30 parts by volume of water. Cooling provides crystals of 7-aza-2-carboxymethyl-6-methoxy-1-tetralone, melting at 174°–176° C.

2.3 Parts of this compound in 50 parts by volume of methanol is esterified by diazomethane generated from 10 parts of nitrosomethylurea in 30 parts by volume of potassium hydroxide and 100 parts by volume of ether. The solution is allowed to set for 0.5 hour room temperature and it is filtered. The solvent is reduced and upon cooling, needles of 7-aza-6-methoxy-2-methoxycarbonylmethyl-1-tetralone are formed, melting at 107°–108.5° C.

Alternatively, 7-aza-6-methoxy-2-carboxymethylidene-1-tetralone is esterified by acid catalysed reaction with methanol to provide 7-aza-6-methoxy-2-methoxycarbonylmethylidene-1-tetralone, melting at 111°–112° C.

1 Part of this compound in 250 parts by volume of ethanol is catalytically reduced over 0.1 part of 5% Pd/Carbon at 54.9 p.s.i. at room temperature to provide upon isolation 7-aza-6-methoxy-2-methoxycarbonylmethyl-1-tetralone.

To 4.05 parts of 7-aza-6-methoxy-2-methoxycarbonylmethyl-1-tetralone in 100 parts by volume of cold methanol is added in portions a total of 1.4 parts of sodium borohydride. The solution is warmed to room temperature and acetone is added. The solution is then reduced to ¼ its volume and precipitation occurs upon the addition of water. The precipitate is crystallized from ethanol to provide methyl 8-hydroxy-3-methoxy-5,6,7,8-tetrahydro-2-azanaphthalene-7-acetate, melting at 92°–96° C.

2.1 Parts of this compound is dissolved in 50 parts by volume of anisole containing 1.0 part of 10% Pd/Carbon and the mixture is refluxed under nitrogen for 6 hours after which time 0.5 part of catalyst is again added and refluxing is continued. This process is repeated until a total of 10.5 parts of catalyst is added. The reaction mixture is cooled, filtered through Celite and washed 2 times with 5% sodium bicarbonate, and 2 times with saturated sodium chloride. Removal of the solvent provides an oil. Chromatography on silica gel using 10% ethyl acetate/benzene as eluant provides methyl 3-methoxy-2-azanaphthalene-7-acetate melting at 49.5°–51° C.

To 1 part of the above indicated ester in 30 parts by volume of tetrahydrofuran is added 1 part of lithium diisopropylamide and the mixture is cooled. To this mixture is added 0.5 part of methyl iodide and the reaction mixture is stirred for 1 hour and allowed to warm to room temperature. The reaction is quenched with ethanol and then water. The reaction mixture is extracted with methylene chloride and the product isolated to provide methyl-3-methoxy-2-azanaphthalene-7-α-methylacetate.

Repeating the -α-alkylation process provides methyl-3-methoxy-2-azanaphthalene-7-α,α-dimethylacetate.

Alternatively the second alkylation may be conducted with 0.5 part of ethyl iodide to provide methyl-3-methoxy-2-azanaphthalene-7-α-methyl-α-ethylacetate.

Hydrolysis of the indicated esters by heating in alcoholic potassium hydroxide provides 3-methoxy-2-azanaphthalene-7-acetic acid, 3-methoxy-2-azanaphthalene-7-α-methylacetic acid, and 3-methoxy-2-azanaphthalene-7-α,α-dimethylacetic acid after acidification. In turn these acids are converted to ethyl esters by acid catalysed esterification with an excess of ethanol. Such esterification provides ethyl 3-methoxy-2-azanaphthalene-7-acetate, ethyl 3-methoxy-2-azanaphthalene-7-α-methylacetate, and ethyl 3-methoxy-2-azanaphthalene-7-α,α-dimethylacetate.

Optical Resolution: 3-Methoxy-2-azanaphthalene-7-α-methylacetic acid is reacted with cinchonidine to form the diastereoisomer salts. Fraction crystallization followed by acid cleavage in dilute hydrochloric acid provides d and 1 3-methoxy-2-azanaphthalene-7-α-methylacetic acid.

Refluxing 1 part of 3-methoxy-2-azanaphthalene-7-acetic acid in 25 parts by volume of 16% hydrobromic acid followed by extraction with methylene chloride and isolation provides 3-hydroxy-2-azanaphthalene-7-acetic acid.

EXAMPLE 26

Reduction of 1 part of methyl 3-methoxy-2-azanaphthalene-7-α-methylacetic acid in 50 parts by volume ethyl ether containing 1 part of lithium aluminum hydride followed by quenching of the reaction with ethyl acetate, washing with saturated sodium chloride, and isolation provides 7-(2-hydroxyethyl)-2-methoxy-2-azanaphthalene.

EXAMPLE 27

To 1 part of methyl 3-methoxy-2-azanaphthaleneacetate in 25 parts by volume of toluene at −78° C. is slowly added 0.33 part of diisobutylaluminum hydride in toluene. The reaction is stirred for 1 hour and allowed to come to room temperature. The reaction is quenched with ethylacetate followed by ice water. The organic layer is washed with saturated sodium chloride, dried with anhydrous sodium sulfate, and 3-methoxy-2-azanaphthaleneacetaldehyde is isolated.

EXAMPLE 28

4.15 Parts of 7-aza-6-methoxy-2-methoxycarbonylmethylidene, melting at 111°–112° C. and described in Example 25 is reduced by 0.4 part of sodium borohydride in 100 parts by volume of cold methanol to provide methyl 8-hydroxy-3-methoxy-5,6,7,8-tetrahydro-2-azanaphthalene-7-methylidenecarboxylate after isolation by the addition of water to the reaction mixture and filtration of the resulting precipitate.

2.3 Parts of this hydroxy ester in 20 parts by volume of tetrahydrofuran is added slowly to a solution of lithium diisopropylamide prepared by reacting 2.3 parts of diisopropylamide with 13 parts by volume of 1.7 molar methyl lithium in ether in 35 parts by volume of tetrahydrofuran at −78° C. and in an inert atmosphere. This reaction mixture may be treated by either of two procedures:

A. Quenched with acetic acid in ether to provide methyl 3-methoxy-2-azanaphthalene-7-acetate or B. By reaction of 0.5 part of methyl iodide to provide methyl 3-methoxy-2-azanaphthalene-7-α-methylacetate as an oil.

Hydrolysis of 1.1 parts of this ester in 15 parts by volume of methanol containing aqueous potassium hydroxide by reflux for 1 hour, followed by cooling, acidification to pH 5, and extraction with ethyl acetate provides 3-methoxy-2-azanaphthalene-7-α-methylacetic acid upon evaporation of the ethyl acetate and recrystallization from methanol. This compound melts at 155.5°–156.5° C.

This acid is conveniently resolved into the d and l optical isomers by mixing a hot solution of 7.15 parts of the above acid in 20 parts by volume of methanol and 5 parts by volume of acetone and 1.5 parts of cinchonidine in 15 parts by volume of methanol and 10 parts by volume of acetone and then cooling the resulting solution. A salt precipitates upon cooling and this salt is filtered and crystallized from methanol-acetone and the free acid is liberated from the salt by shaking with a mixture of dilute hydrochloric acid and benzene. Evaporation of the benzene layer and crystallization of the residue from acetone-hexane provides d-α-methyl-2-azanaphthalene-7-α-methylacetic acid, the d enantiomer. Acidification of the mother liquor from the cinchonidine salt solution provides the l enantiomer, 1-3-methoxy-2-azanaphthalene-7-α-methyl acetic acid.

EXAMPLE 29

11 Parts of 8-hydroxy-3-methoxy-5,6,7,8-tetrahydro-2-azanaphthalene-7-acetate described in Example 25 is added to 110 parts by volume of sulfuric acid at room temperature and stirred for 15 minutes. 200 Parts of ice water are added and the solution is made basic with 300 parts by volume of aqueous ammonia. The solution is filtered through celite and then extracted three times with chloroform. Removal of the chloroform and crystallization from methanol provides 3-methoxy-7,8-dihydro-2-azanaphthalene-7-acetic acid, melting at 151°–152° C. This compound is also an active anti-inflammatory agent, as is the alkylated derivative, 3-methoxy-7,8-dihydro-2-azanaphthalene-7-α-methylacetic acid.

What we claim is:

1. A compound of the formula

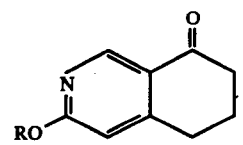

wherein R represents alkyl having 1 to 4 carbon atoms.

2. As in claim 1, the compound which is 7-aza-6-methoxy-1-tetralone.

* * * * *